United States Patent [19]

Nakanishi et al.

[11] Patent Number: 5,260,301
[45] Date of Patent: Nov. 9, 1993

[54] PHARMACEUTICAL SOLUTION CONTAINING FK-506

[75] Inventors: Shigeo Nakanishi, Neyagawa; Iwao Yamanaka, Osaka, both of Japan

[73] Assignee: Fujisawa Pharmaceutical Co., Ltd., Osaka, Japan

[21] Appl. No.: 984,239

[22] Filed: Dec. 1, 1992

Related U.S. Application Data

[63] Continuation of Ser. No. 662,443, Feb. 28, 1991, abandoned.

Foreign Application Priority Data

Mar. 1, 1990 [JP] Japan .................. 2-51110

[51] Int. Cl.$^5$ ............... A61K 31/44; A61K 47/00
[52] U.S. Cl. ...................... 514/291; 514/294; 514/786; 514/789; 514/943; 514/970; 514/975
[58] Field of Search ............. 514/291, 294, 786, 789; 424/554, 555

[56] References Cited

U.S. PATENT DOCUMENTS

| | | | |
|---|---|---|---|
| 3,997,590 | 12/1976 | Lester | 260/470 |
| 4,082,780 | 4/1978 | Miki et al. | 514/182 |
| 4,894,366 | 1/1990 | Okuhara et al. | 514/63 |
| 5,023,262 | 6/1991 | Caufield et al. | 514/291 |
| 5,064,835 | 11/1991 | Bochis et al. | 514/21 |

FOREIGN PATENT DOCUMENTS

| | | |
|---|---|---|
| 0323042 | 7/1989 | European Pat. Off. |
| 61-148181 | 4/1986 | Japan . |

*Primary Examiner*—Frederick E. Waddell
*Assistant Examiner*—T. J. Criares
*Attorney, Agent, or Firm*—Oblon, Spivak, McClelland, Maier & Neustadt

[57] ABSTRACT

A pharmaceutical solution which contains the compound of the general formula having the immusuppreseive activity is disclosed.

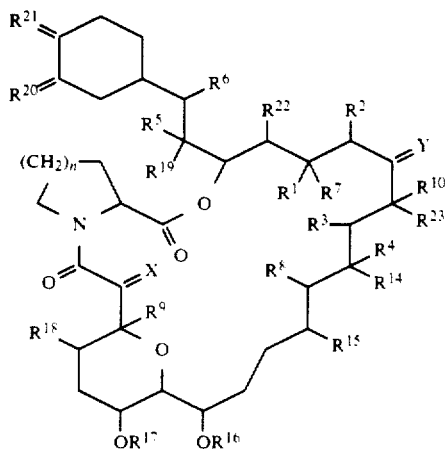

8 Claims, No Drawings

PHARMACEUTICAL SOLUTION CONTAINING FK-506

This application is a continuation of application Ser. No. 07/662,443, filed on Feb. 28, 1991, now abandoned.

FIELD OF THE INVENTION

The present invention relates to a pharmaceutical solution which contains the compound (I) or a pharmaceutically acceptable salt thereof described later that is known as showing immunosuppressive activity.

In detail, the present invention relates to the solution which shows long term storage stability in a nonaqeuous solution and may be diluted with such as physiological saline, glucose solution for injection, water, fruit juice, and the like without occurence of any precipitations of the compound(I).

Accordingly, the present invention relates to the above pharmaceutical solution which can be applied for various form of medicine such as intravenous injection, oral administrating liquidous medicine, or the like.

Prior Arts

The compound(I) used in the present invention is shown as follows.

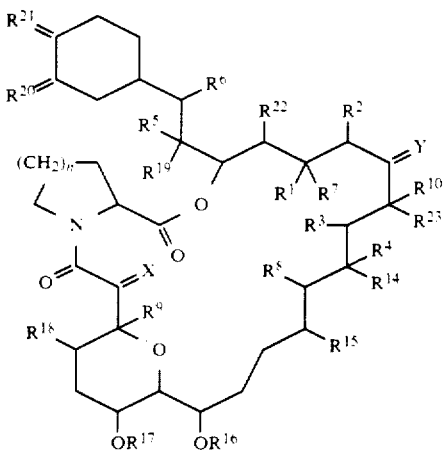

(I)

wherein each vicinal pair of substituents [$R^1$ and $R^2$], [$R^3$ and $R^4$], [$R^5$ and $R^6$] independently a) represent two vicinal hydrogen atoms, or b) form a second bond between the vicinal carbon atoms to which they are attached;

in addition to its significance above, $R^2$ may represent an alkyl group;

$R^7$ represents H, OH, protected hydroxy or O-alkyl, or in conjunction with $R^1$ it may represent =O;

$R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O (H,OH), (H,H) or —$CH_2O$—;

Y represents O, (H,OH), (H,H) or N—$NR^{11}R^{12}$ or N—$OR^{13}$;

$R^{11}$ and $R^{12}$ independently represent H, alkyl, aryl or tosyl;

$R^{13}$, $R^{14}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a, H) and ($R^{21}$a, H) respectively; $R^{20}$a and $R^{21}$a independently represent OH, O-alkyl or $OCH_2OCH_2CH_2OCH_3$ or $R^{21}$a is protected hydroxy;

in addition, $R^{20}$a and $R^{21}$a may together represent an oxygen atoms in an epoxide ring;

n is 1, 2 or 3;

in addition to their significances above, Y, $R^{10}$ and $R^{23}$, together with the carbon atoms to which they are attached, may represent a 5- or 6- membered N-, S- or O-containing heterocyclic ring, which may be saturated or unsaturated, and which may be substistuted by one or more groups selected from alkyl, hydroxy, alkyl substituted by one or more hydroxyl groups, O-alkyl, benzyl and —$CH_2Se(C_6H_5)$.

The compound (I) and its pharmaceutically acceptable salt have remarkable immunosuppressive, antimicrobial and other pharmacologic activities and are known to be of value in the treatment and prevention of resistance to organ or tissue transplantation, graft-versus-host disease, various autoimmune disease and infectious disease (Japanese Kokai Patent Publication No. 61-148181/1986 and European Patent Publication No.0323042).

Such compound(I) and its pharmaceutically acceptable salt are prepared in the same manner as the one described in the above-mentioned two patent applications. Particularly, the macrolides, which are produced by fermentation of *Streptmyces tsukubaensis* No.9993 (FERM BP-927) or *Streptmyces hygroscopicus* subsp. *yakushimaensis* No.7238 (FERM BP-928), are numbered FR-900506, FR-900520, FR-900523 and FR-900525.

It is considered to prepare various kind forms of medicine such as powder, suspension, pharmaceutical solution which contains the compound (I) and pharmaceutically acceptable salt thereof (hereinafter the term "compound (I)" is representatively used to show them). However it is difficult to prepare stable pharmaceutical solution of the compound(I), which causes a difficulty in applying the compound (I) for clinical use where it is desired to prepare pharmaceutical solution e.g., injection, oral administrating liquid, local scattering solution, dropping lotion in the eye, and the like.

Object of the Invention

It is the object of the present invention to prepare pharmaceutical solution containing the compound (I).

In more detail it is the object of the present invention to prepare the above pharmaceutical solution which shows clear aqueous solution state that is especially desired for intravenous injection.

SUMMARY OF THE INVENTION

Pharmaceutical solution of the present invention comprises of the above compound (I) as an active ingredient, a pharmaceutically acceptable surface active agent and nonaqueous solvent.

DETAILED DESCRIPTION OF THE INVENTION

In the above and subsequent descriptions on the present invention, suitable examples and illustrations of the various definitions which the present invention includes within the scope thereof are explained in detail as follows.

The term "lower" as used in this specification means, unless otherwise indicated, any number of carbon atoms between 1 and 6, inclusive.

Suitable "alkyl" means straight or branched saturated aliphatic hydrocarbon residue and may include lower alkyl such as methyl, ethyl, propyl, isopropyl, butyl, isobutyl, pentyl, neopentyl, hexyl, and the like.

Suitable "alkenyl" means straight or branched unsaturated aliphatic hydrocarbon residue having one double bond and may include lower alkenyl such as vinyl, propenyl, butenyl, metylpropenyl, pentenyl, hexenyl, and the like.

Suitable "aryl" may include phenyl, tolyl, xylyl, cumenyl mesityl, naphthyl, and the like.

Suitable examples of the protective group in the "protected hydroxyl group" may include:

1-(lower alkylthio)(lower)alkyl groups such as lower alkylthiomethyl groups (e.g. methylthiomethyl, ethylthiomethyl, propylthiomethyl, isopropylthiomethyl, butylthiomethyl, isobutylthiomethyl, hexylthiomethyl, etc.), more desirably $C_1$-$C_4$ alkylthiomethyl groups, and most desirably methylthiomethyl; tri-substitueted silyl groups such as tri(lower)-alkylsilyl groups (e.g. trimethylsilyl, triethylsilyl, tributylsilyl, tert-butyl-dimethylsilyl, tri-tert-butylsilyl, etc.); lower alkyl-diarylsilyl groups (e.g. methyldiphenylsilyl, ethyldiphenylsilyl, propyldiphenylsilyl, tert-butyldiphenylsilyl, etc.), more desirably tri($C_1$-$C_4$)alkylsilyl and $C_1$-$C_4$ alkyldiphenylsilyl groups and most desirably tert-butyldimethylsilyl and tert-butyldiphenylsilyl; and acyl groups such as aliphatic acyl groups, aromatic acyl groups and aliphatic acyl groups substituted by aromatic groups, which are derived from carboxylic acids, sulfonic acids or carbamic acids.

The aliphatic acyl group may includes lower alkanoyl groups which may optionally have one or more suitable substituents such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo(lower)alkoxy - (lower)alkanoyl groups which may optionally have one or more appropriate substituents such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.), camphorsulfonyl, lower alkylcarbamoyl groups having one or more suitable substituents such as carboxy or protected carboxy, for example carboxy(lower)alkylcarbamoyl groups( e.g. carboxymethylcarbamoyl, carboxyethylcarbamoyl, carboxypropylcarbamoyl, carboxybutylcarbamoyl, carboxypentylcarbamoyl, carboxyhexylcarbamoyl, etc. , protected caroxy(lower)alkylcarbamoyl groups suc as tri(lower)alkylsilyl(lower)alkoxycarbonyl(lower)alkylcarbamoyl groups (e.g. trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

The aromatic acyl group may include aroyl groups which may optionally have one or more suitable substituents such as nitro (e.g. benzoyl, toluoyl, xyloyl, naphthoyl, nitrobenzoyl, dinitrobenzoyl, nitronaphthoyl, etc., arenesulfonyl groups which may optionally have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.), and so on.

The aromatic group-substituted aliphatic acyl groups may include ar(lower)alkanoyl groups which may optionally have one or more suitable substituent(s) such as lower arkoxy and trihalo(lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc. , and so on.

Among the above-mentioned acyl groups, the more desirable acyl groups are $C_1$-$C_4$ alkanoyl groups which may optionally be substituted by carboxy, cyclo($C_5$-$C_6$-)alkyloxy($C_1$-$C_4$)alkanoyl groups having two ($C_1$-$C_4$)alkyl groups in the cycloalkyl moiety, camphorsulfonyl, carboxy($C_1$-$C_4$)alkylcarbamoyl groups, tri($C_1$-$C_4$) alkylsilyl($C_1$-$C_4$)alkoxycarbonyl($C_1$-$C_4$)alkylcarbamoyl groups, benzoyl which may have one or two nitro groups, halogen-substituted benzenesulfonyl groups, phenyl($C_1$-$C_4$)alkanoyl groups having $C_1$-$C_4$ alkoxy and trihalo($C_1$-$C_4$)alkyl groups. Of these groups, the most desirable are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Suitable "5- or 6-membered N-, S- or O- containing heterocyclic ring" may include pyrrolyl, tetrahydrofuryl, and the like.

The pharmaceutically acceptable salt of compound (I) is a nontoxic salt, which may be the corresponding salt with an inorganic or organic base such as alkali metal salts (e.g. sodium salt, potassium salt, etc.), ammonium salt and amine salts (e.g. triethyamine salt, N-benzyl-N-methylamine salt, etc.), and so on.

With regard to the compound 1 of the present invention, it is to be noted that there may be one or more than one conformers on stereoisomers such as optically or geometrically isomeric pairs due to the presence of one or more than one assymetric carbon atom or double bond, and these are included within a scope of the compound (I) of the present invention.

It will hereinafter be described in detail how the present invention has completed, especially relating to the important point of the present invention i.e., the reason why a mixture of surface active agent and nonaqueous solvent is selected in this invention.

A liquidous pharmaceutical containing the compound (I) should be offered as a stable liquid as it is for the purpose of administrating to human body and transferring the effective amount of the ingredient compound to human body. Further on considering a special use such as intravenous injection that is the main object of the present invention, should be offered a whole clear liquidous pharmaceutical which can maintain the clearity under long term storage.

From the above point of view, the inventors of the present invention studied, at first, the solubility of the compound (I) in water. As a test compound, the inventors selected the following compound as a free form which has an excellent immunosuprressive activity and is called FK 506 hereafter.

| | |
|---|---|
| $R^1$, $R^2$, $R^8$, $R^{23}$ = hydrogen | $R^7$, $R^9$ = hydroxy |
| $R^{14}$, $R^{15}$, $R^{16}$, $R^{17}$, $R^{18}$, $R^{19}$, $R^{22}$ = methyl | $R^{10}$ = allyl |
| $R^{20}$ = $R^{20}$ a, H ($R^{20}$ a = methoxy) | X, Y = oxygen |
| $R^{21}$ = $R^{21}$ a, H ($R^{21}$ a = hydroxy) | n = 2 |
| $R^3$, $R^4$ = form a second bond between the vicinal carbon atoms to which they are attached | |
| $R^5$, $R^6$ = form a second bond between the vicinal carbon atoms | | to which they are attached

The solubility of FK 506 in water is at most 3 μg/ml under ambient temperature. Accordingly, it is decided to add a surface active agent in order to increase the solubility of FK 506 in water to the level where the clinically effective amount of FK 506 is dissloved. Table 1 shows the solubility of FK 506 under the different condition e.g., the kind and the concentration of a surface active agent and temperature. As a surface active agent, a castor oil-surface active agent i.e., HCO-10, HCO-40, HCO-60 (trademark, prepared by Nikko Chemicals, respectively) are selected for examination.

It is conjectured from the result shown in Table 1 that the concentration of the surface active agent should be controlled at 1.43w/v% [about 150 mg of the surface active agent against 1 mg of FK506] to dissolve 0.1 mg of FK 506 in 1 ml of water, calculating based on the result that 0.035 mg of FK 506 is dissolved in 1 ml of 0.5w/v% HCO-60 aqueous solution at 20° C. Accordingly, if it is desired to prepare 5 mg/ml aqueous solution FK 506, the concentration of the surface active agent is estimated to come up to 87w/v% from the calculation based on the result of HCO-60, 20w/v%, 20° C. Such tolerably high concentration of surface active agent in aqueous solution should not be realized in practice of clinical field.

TABLE 1

| Concentration of surface active agent (w/v %) | Kind of surface active agent and solubility of FK506 (mg/ml) | | | | |
|---|---|---|---|---|---|
| | HCO-40 | HCO-60 | | Mixture of HCO-60 and HCO-10 (4:1) | |
| | 20° C. | 20° C. | 30° C. | 20° C. | 30° C. |
| 0.1 | — | 0.005 | — | — | — |
| 0.3 | — | 0.019 | — | — | — |
| 0.5 | — | 0.035 | — | — | — |
| 5 | 0.40 | 0.28 | 0.29 | 0.26 | 0.27 |
| 10 | 0.78 | 0.61 | 0.57 | 0.56 | 0.56 |
| 20 | 1.52 | 1.15 | 1.14 | 1.13 | 1.14 |

HCO-60: Polyoxyethylenehydrogenated Castor Oil 60
HCO-40: Polyoxyethylenehydrogenated Castor Oil 40
HCO-10: Polyoxyethylenehydrogenated Castor Oil 10

Table 2 shows a remaining percentage of FK 506 in aqueous solution wherein FK 506 is dissolved in water in the presence of large amount of surface active agent. From this table, it is found that the stability for long period storage is not expectable in the above prescription.

TABLE 2

| | Remaining percentage of FK 506 (%) (prescription) | |
|---|---|---|
| Storage conditions | FK 506 HCO-60 phosphoric acid buffer (pH 6) | 0.5 mg 100 mg 1 ml |
| Initial | 100.0 | |
| After 3 days (at 40° C.) | 52.7 | |
| After 3 days (at 60° C.) | 42.2 | |

From the results of the above experiment, it is recognized that the use of surface active agent is not profitable means for the purpose of dissolving the compound (I), for example FK 506, in water.

Table 3 shows solubility of FK 506 in several kinds of nonaqueous solvent such as PEG (polyethylene glycol) 400, ethanol and propylene glycol. From the consideration of the illustrated data, it is found that PK 506 is dissolved in the experimented solvent at the concentration of more than 40 mg/ml.

TABLE 3

| Solvent | Solubility (at ambient temperature) |
|---|---|
| Ethanol | >300 |
| PEG 400 | >40 |
| Propylene glycol | >40 |
| | (mg/ml) |

Nonaqueous solvent is, at the time of administrating into the human vascular tract, usually diluted with aqueous solvent such as physiological saline, since nonaqueous solvent has hemolysis action. Therefore, the inventors of the present invention diluted the experimental solution by using nonaqueous solution (1 ml) described in the following prescriptions 1 & 2 with physiological saline (100 ml), and it was found that the nonaqeuous solution became turbid at once and fine crystal of FK 506 was precipitated in a mixed medium.

| (Prescription 1) | |
|---|---|
| FK 506 | 10 mg |
| Ethanol to | 1 ml |
| (Prescription 2) | |
| FK 506 | 10 mg |
| Propylene glycol to | 1 ml |

Standing on the above result, the inventors of the present invention have then studied on combination use of nonaqueous solvent and surface active agent.

The experimental solution (1 ml) of the following prescription 3 consisting of FK 506, surface active agent and nonaqueous solvent was diluted with physiological saline (100 ml) to find that the clear appearance of prescription was kept unchange.

| (Prescription 3) | |
|---|---|
| FK 506 | 10 mg |
| HCO-60 | 100 mg |
| Ethanol to | 1 ml |

Then several prescriptions of clear solution were further prepared altering the concentration of FK 506, the kind and the concentration of surface active agent, and were tested how change the clearity of the solution and whether separate out the crystal or not under the several condition of different degree of dilution. The results thereof are shown in Table 4.

TABLE 4

| Concentration of FK 506 (mg/ml) | Dilution times with physiological saline | Period till solution becomes turbid to crystallize FK506 (in days) Kind of surface active agent/Ratio of ethanol to surface active agent | | | | | | |
|---|---|---|---|---|---|---|---|---|
| | | HCO-60 | | | Cremophor ® EL | | HCO-40 | |
| | | 35/65 | 60/40 | 80/20 | 35/65 | 80/20 | 40/60 | 80/20 |
| 5 | 2 | ≧7 | ≧7 | ≧7 | ≧7 | ≧7 | ≧7 | ≧7 |
|   | 100 | ≧7 | ≧7 | ≧7 | ≧7 | ≧7 | ≧7 | ≧7 |
| 10 | 2 | ≧7 | ≧7 | ≧7 | ≧7 | ≧7 | ≧7 | ≧7 |
|   | 100 | ≧7 | ≧7 | ≧7 | ≧7 | ≧7 | ≧7 | ≧7 |
| 25 | 2 | ≧7 | ≧7 | ≧7 | ≧7 | ≧7 | ≧7 | ≧7 |
|   | 100 | ≧7 | ≧1 | ≧7 | ≧7 | ≧1 | ≧7 | ≧1 |
| 50 | 2 | ≧7 | ≧7 | ≧7 | ≧7 | ≧1 | ≧7 | ≧1 |

Cremophor ® EL: trademark, prepared by BASF (Polyoxyethylene Castor Oil 35)

It is concluded from the result illustrated in Table 4 that a clear pharmaceutical solution which does not cause Precipitation of the compound (I) on diluting with physiological saline can be prepared by controlling the ratio of the compound(I), surface active agent and nonaqueous solvent according to the kind of surface active agent under the condition that the concentration of the compound (I) is less than 50 mg/ml.

Lastly it is tested the remaining percentage of FK 506 after storage in nonaqueous solvent containing both FK 506 and surface active agent. In the test solution, the concentration of FK 506 is adjusted to 5 mg/ml, and, for comparative a nonaqueous solution which contain only FK 506 is prepared. The experimental result is shown in Table 5.

TABLE 5

| Storage conditions | | Remaining percentage of FK 506(%) (prescription) |
|---|---|---|
| | | FK 506       5 mg |
| | | HCO-60       400 mg |
| | | ethanol to   1 ml |
| Initial | | 100.0 |
| 80° C | 1 day | 95.2 |
| | 3 day | 90.4 |
| | 5 day | 86.4 |
| | 10 day | 78.6 |
| | 17 day | 68.0 |
| 60° C | 5 day | 96.4 |
| | 10 day | 95.1 |
| | 17 day | 92.4 |
| | 1 month | 88.0 |
| 40° C | 1 month | 96.7 |
| | 3 month | 96.6 |
| | 18 month | 84.6 |

It is concluded from the result shown in table 5 that HCO-60 is the most preferable surface active agent in the view point of storage stability.

As considered from the above experiments, the compound (I) such as FK 506 has quite poor solubility in water and this is not so improved even in the presence of surface active agent, and the storage stability especially at ambient temperature is quite inferior excepting that only frozen one can stand for some period of time.

In the mean time, it is found that the compound (I) is well dissolved in nonaqueous solvent. However it causes precipitation of the compound (I) on diluting with physiological saline to diminishing hemolysis action of nonaqueous solvent. Occurence of precipitation makes it impossible to use in the clinical field.

Under the condition of cooperative use of nonaqueous solvent and surface active agent, it is noted that the compound (I) is well dissolved and there is no problem after long pereiod storage, and further it does not happen to give any Precipitate at the time of diluting with physiological saline.

The kind of nonaqueous solvent is not limited in the present invention, and any nonaqueous solvent may be used as much as it can dissolve the effective amount of the compound (I) and it may be acceptable in clinical use. The nonaqueous solvent may be used either alone or as a mixture thereof. Suitable examples thereof include ethanol, propylene glycol, glycerin, Polyethylene glycol (e.g., PEG 400, PEG 300, PEG 200, etc.), or the mixture thereof from a view point of solubility and viscosity, etc. and most preferable one is ethanol. The representative examples of the surface active agent include, from a view point of storage stability for long term, a castor oil-surface active agents, and more preferable one is HCO (polyoxyethylene hardened oil)-surface active agents, and most preferable one is HCO-60, HCO-50 and the like. In addition to the above exemplified surface active agents, polyoxyethylene sorbitane fatty acid ester derivative (e.g., Polysorbate 80, etc.,), glycerine fatty acid ester derivative (e.g., glycerine monocaprylate, etc.), polyethylene glycol fatty acid ester derivative (e.g., polyoxyethylene 40 monostearate, etc.), and the like may also be used.

The concentration of the compound (I) is determined from the judgement including the kind and the concentration of nonaqueous solvent and surface active agent, the composition ratio thereof, the stability after being diluted with physiological saline, etc. and storage stability. The suitable range of thus determined concentration is usually in the range of 0.1 ~ 50 mg/ml and more preferably 1 ~ 20 mg/ml.

As for the amount of surface active agent, it is noted to be less than the calculated estimation. From the experimental calculation based on the result illustrated in Table 1, about 150 mg of the surface active agent may be necessary to obtain a saturated aqueous solution containing 1 mg of the compound (I) as stated above. However in the present invention the compound (I) is dissolved in a mixed solution of nonaqueous solvent—surface active agent—water to form stable supersaturation state, and therefore the necessary amount of surface active agent becomes less than the calculated one. These specific action, i.e., the low precipitating speed of the crystalline from the supersaturated solution, is based on the characteristic property of the compound (I). The range of the ratio of surface active agent to the compound (I) is preferably 1 ~ 100 mg/1 mg. and more preferably 30 ~ 60 mg/1 mg to prevent the occurence of precipitation at the time of diluting for clinical use.

The pharmaceutical solution of the present invention may further contain, if necessary, other agent such as stabilizing agent, anodyne, and the like.

The pharmaceutical solution of the present invention is stable during long term storage and does not occur the precipitation of crystalline at the time of dilution.

Therefore, this is applicable to various kind of medicine form such as intravenous injection, dropping lotion in the eye, dropping lotion in the nose, intraenteric injection, percutaneous liniment, local scattering agent, oral administration agent (e.g., syrup, etc.), and the like.

EXAMPLE

Following prescriptions are shown only for the purpose of the explanation of this invention.

| Prescription 1 | |
| --- | --- |
| FK 506 | 10 mg |
| HCO-60 | 400 mg |
| Ethanol to | 1 ml |

The solution comprising the ingredients stated above is prepared by dissolving the FK 506 and HCO-60 in ethanol by a conventional manner.

The following solutions are also prepared a similar manner of the Prescription 1.

| Prescription 2 | |
| --- | --- |
| FK 506 | 5 mg |
| HCO-40 | 200 mg |
| PEG 400 to | 1 ml |
| Prescription 3 | |
| FK 506 | 2 mg |
| Polysorbate 80 | 50 mg |
| Propylene glycol to | 1 ml |
| Prescription 4 | |
| FK 506 | 2 mg |
| Polysorbate 80 | 10 mg |
| Glycerine | 0.5 ml |
| Ethanol to | 1 ml |
| Prescription 5 | |
| FK 506 | 2 mg |
| HCO-60 | 20 mg |
| Propylene glycol to | 1 ml |
| Prescription 6 | |
| FK 506 | 1 mg |
| Polyoxyethylene (40) mono stearate | 20 mg |
| Propylene glycol to | 1 ml |
| Prescription 7 | |
| FK 506 | 10 mg |
| HCO-60 | 400 mg |
| Ethanol to | 1 ml |
| Prescription 8 | |
| FK 506 | 5 mg |
| HCO-60 | 400 mg |
| Ethanol to | 1 ml |
| Prescription 9 | |
| FK 506 | 25 mg |
| HCO-60 | 400 mg |
| Ethanol to | 1 ml |
| Prescription 10 | |
| FK 506 | 2 mg |
| HCO-60 | 10 mg |
| Glycerine | 0.5 ml |
| Ethanol to | 1 ml |

Effect of the Invention

Thus obtained nonaqueous pharmaceutical solution containing the compound (I) is stable during long term storage and does not occur any precipitation at the time of diluting with physiological saline, glucose solution for injection, water, fruit juice, milk, or the like for clinical use. Accordingly, the pharmaceutical solution of the present invention is applicable to various kind of medicine form such as intravenous injection, oral administration agent and the like, which could contribute the compound (I) in clinical field wherein its immunosuppressive activity is intensely desired. Paticularly, the most preferable medicine form of the present nonaqueous pharmaceutical solution is the one for intravenous injection by diluting with the physiological saline.

What we claim:

1. A pharmaceutical solution which comprises FK 506, a pharmaceutically acceptable surface active agent comprising polyoxyethylene hydrogenated castor oil, and a pharmaceutically acceptable nonaqueous solvent selected from the group consisting of ethanol, pyropylene glycol, glycerin and polyethylene glycol.

2. The pharmaceutical solution of claim 1, wherein the FK 506 and the pharmaceutically acceptable surface active agent are in the ratio of 1:1 to 1:100 by weight.

3. The pharmaceutical solution of claim 1, wherein the pharmaceutically acceptable nonaqueous solvent is propylene glycol.

4. The pharmaceutical solution of claim 1, wherein the pharmaceutically acceptable nonaqueous solvent is glycerin.

5. The pharmaceutical solution of claim 1, wherein the pharmaceutically acceptable nonaqueous solvent is polyethylene glycol.

6. The pharmaceutical formulation of claim 1, wherein the polyoxyethylene hydrogenated castor oil is polyoxyethylene hydrogenated Castor Oil 60.

7. The pharmaceutical solution of claim 1 wherein the pharmaceutically acceptable nonaqueous solvent is ethanol.

8. A process for preparing a pharmaceutical solution, which comprises mixing FX 506 and a pharmaceutically acceptable surface active agent comprising polyoxyethylene hydrogenated caster oil in a pharmaceutically acceptable nonaqueous solvent selected from the group consisting of ethanol, propylene glycol, glycerin and polyethylene glycol.

* * * * *

UNITED STATES PATENT AND TRADEMARK OFFICE
CERTIFICATE OF CORRECTION

PATENT NO. : 5,260,301  Page 1 of 4

DATED : NOVEMBER 9, 1993

INVENTOR(S) : SHIGEO NAKANISHI et al

It is certified that error appears in the above-identified patent and that said Letters Patent is hereby corrected as shown below:

On title page, item [57], second line under Abstract. "immusuppreseive" should read --immunosuppressive--.

Column 1, line 20, "various form" should read --various forms--.

Column 3, lines 19-20, "etc.), more desirably $C_1$-$C_4$ alkylthiomethyl groups, and most desirably" should read --etc.), more desirably $C_1$-$C_4$ alkylthiomethyl groups, and most desirably--;

line 33, "may includes lower" should read --may include lower--;

line 51, "groups suc as" should read --groups such as--;

line 63, "etc., arenesulfonyl" should read --etc.), arenesulfonyl--.

Column 5, line 51, "large amount of" should read --large amounts of--.

Column 6, line 2, "use of surface" should read --use of a surface--;

UNITED STATES PATENT AND TRADEMARK OFFICE
CERTIFICATE OF CORRECTION

PATENT NO. : 5,260,301
DATED : NOVEMBER 9, 1993
INVENTOR(S) : SHIGEO NAKANISHI et al

It is certified that error appears in the above-identified patent and that said Letters Patent is hereby corrected as shown below:

Column 6, line 9, "PK 506" should read --FK 506--;

line 52, "was kept unchange." should read --was kept unchanged.--;

lines 60-68 delete in its entirety, insert --Then several prescriptions of clear solution were further prepared altering the concentration of FK 506, the kind and the concentration of surface active agent, which were tested for a change of the clarity of the solution and whether there was separation of the crystal or not under the several condition of different degree of dilution. The results thereof are shown in Table 4.--

Column 7, line 27, "which contain" should read --which contains--;

line 57, "frozen one can" should read --frozen ones can--.

Column 8, line 24, "and most preferable" should read --and the most preferable--;

line 27, "active agents" should read --active agent--;

UNITED STATES PATENT AND TRADEMARK OFFICE
CERTIFICATE OF CORRECTION

PATENT NO. : 5,260,301

DATED : NOVEMBER 9, 1993

INVENTOR(S) : SHIGEO NAKANISHI et al

It is certified that error appears in the above-identified patent and that said Letters Patent is hereby corrected as shown below:

Column 8, line 54, "amount ofsurface" should read --amount of surface--;

line 56, "These specific" should read --The specific--;

line 57, "thecrystalline" should read --the crystalline--;

line 64, "other agent such" should read --other agents such--;

line 67, "does not occur" should read --does not suffer from--.

Column 9, lines 1-2, "various kind of medicine form such" should read --various kinds of medicine forms such--;

line 21, "prepared a similar" should read --prepared in a similar--.

UNITED STATES PATENT AND TRADEMARK OFFICE
CERTIFICATE OF CORRECTION

PATENT NO. : 5,260,301
DATED : NOVEMBER 9, 1993
INVENTOR(S) : SHIGEO NAKANISHI et al

It is certified that error appears in the above-identified patent and that said Letters Patent is hereby corrected as shown below:

Column 10, line 14-15, "various kind of medicine form such" should read --various kinds of medicine forms such--;
line 48, "FX 506" should read --FK 506--.

Signed and Sealed this

Fourteenth Day of March, 1995

BRUCE LEHMAN

Attest:

*Attesting Officer*        *Commissioner of Patents and Trademarks*